United States Patent [19]

Evans et al.

[11] Patent Number: 5,032,591

[45] Date of Patent: Jul. 16, 1991

[54] PHARMACEUTICAL PREPARATIONS

[75] Inventors: John M. Evans; Robin E. Buckingham, both of Harlow, England

[73] Assignee: Beecham Group p.l.c., United Kingdom

[21] Appl. No.: 293,209

[22] Filed: Jan. 4, 1989

[30] Foreign Application Priority Data

Jan. 6, 1988 [GB] United Kingdom ............... 8800199

[51] Int. Cl.$^5$ ................. A61K 31/50; A61K 31/495; A61K 31/53; A61K 31/47

[52] U.S. Cl. .................... 514/254; 514/241; 514/242; 514/243; 514/311; 514/312; 514/313; 514/314; 514/307; 514/308; 514/309; 514/310; 514/311; 514/320; 514/337; 514/353; 514/362; 514/363; 514/364; 514/365; 514/369; 514/370; 514/374; 514/376; 514/377; 514/378; 514/380; 514/397; 514/403; 514/413; 514/422; 514/454; 514/455; 514/456

[58] Field of Search ............ 514/422, 620, 254, 241, 514/242, 243, 311-314, 307-310, 320, 337, 362-365, 353, 369-370, 374, 376-378, 380, 397, 403-414, 422, 454, 455, 456

[56] References Cited

U.S. PATENT DOCUMENTS

| 4,446,113 | 5/1984 | Evans et al. | 514/320 |
|---|---|---|---|
| 4,481,214 | 11/1984 | Evans | 514/456 |
| 4,496,565 | 1/1985 | Evans et al. | 514/222 |
| 4,510,152 | 4/1985 | Faruk | 514/422 |
| 4,542,149 | 9/1985 | Evans et al. | 514/422 |
| 4,555,509 | 11/1985 | Evans et al. | 514/456 |
| 4,571,406 | 2/1986 | Evans et al. | 514/456 |
| 4,575,511 | 3/1986 | Evans et al. | 514/456 |
| 4,610,992 | 9/1986 | Evans et al. | 514/422 |
| 4,629,734 | 12/1986 | Ashwood | 514/422 |
| 4,677,116 | 6/1987 | Evans | 514/456 |
| 4,687,779 | 8/1987 | Evans | 514/456 |
| 4,738,963 | 4/1988 | Hamilton et al. | 514/422 |
| 4,772,603 | 9/1988 | Evans | 514/422 |
| 4,782,083 | 11/1988 | Cassidy et al. | 514/422 |
| 4,786,639 | 11/1988 | Evans | 514/422 |
| 4,812,459 | 3/1989 | Evans et al. | 514/254 |
| 4,831,050 | 5/1989 | Cassidy et al. | 514/422 |

FOREIGN PATENT DOCUMENTS

| 0076075 | 4/1983 | European Pat. Off. . |
|---|---|---|
| 0091748 | 10/1983 | European Pat. Off. . |
| 0093535 | 11/1983 | European Pat. Off. . |
| 0095316 | 11/1983 | European Pat. Off. . |
| 0107423 | 5/1984 | European Pat. Off. . |
| 0120426 | 10/1984 | European Pat. Off. . |
| 0120427 | 10/1984 | European Pat. Off. . |
| 0126311 | 11/1984 | European Pat. Off. . |
| 0126350 | 11/1984 | European Pat. Off. . |
| 0126367 | 11/1984 | European Pat. Off. . |
| 0138134 | 4/1985 | European Pat. Off. . |
| 0173848 | 3/1986 | European Pat. Off. . |
| 0176689 | 4/1986 | European Pat. Off. . |
| 0205292 | 12/1986 | European Pat. Off. . |
| 0207614 | 1/1987 | European Pat. Off. . |
| 0214818 | 3/1987 | European Pat. Off. . |
| 0250077 | 12/1987 | European Pat. Off. . |
| 0273262 | 12/1987 | European Pat. Off. . |
| 0277611 | 1/1988 | European Pat. Off. . |
| 0277612 | 1/1988 | European Pat. Off. . |
| 0271271 | 6/1988 | European Pat. Off. . |
| WO87/07607 | 12/1987 | PCT Int'l Appl. . |
| 1489879 | 10/1977 | United Kingdom . |

OTHER PUBLICATIONS

Goodman et al., *The Pharmacological Basis of Therapeutics, Seventh Edition*, pp. 800-801 (1985).
Chemical Abstracts, vol. 108, No. 1, Jan. 4, 1988.

*Primary Examiner*—John W. Rollins
*Attorney, Agent, or Firm*—Jacobs & Jacobs

[57] ABSTRACT

A pharmaceutical product comprising a potassium channel activator antihypertensive agent and a β-blocker antihypertensive agent as a combined preparation for simultaneous, separate or sequential use in therapy of hypertension.

17 Claims, No Drawings

PHARMACEUTICAL PREPARATIONS

The present invention relates to pharmaceutical preparations having antihypertensive activity.

EP-A-173848 (Beecham Group p.l.c.) describes the use of various benzopyran compounds, previously disclosed as antihypertensives, which are potassium channel activators useful in the treatment of cardiovascular disorders.

EP-A-205292 (Beecham Group p.l.c.) discloses a group of pyranopyridines which are also potassium channel activators, useful in the treatment of hypertension, cardiovascular disorders and disorders associated with smooth muscle contraction.

EP-A-214818 and 250077 (Beecham Group p.l.c.) describe further groups of benzopyran derivatives which are potassium channel activator antihypertensive agents.

U.K. Patent No. 1489879 discloses the compound N''-cyano-N-4-pyridyl-N'-1,2,2-trimethylpropylguanidine and, in Example 47, a process by which it can be prepared. The compound, which is referred to herein by its common name, pinacidil, is described in the patent as a hypotensive compound. In "Drugs of the Future" Vol. VI(3), 149, 981, pinacidil is described as a vasodilator. It is now known that pinacidil is a potassium channel activator.

EP-A-112776 (Rhône-Poulenc Santé) discloses the compound N-methyl-2-(3-pyridinyl)-tetrahydrothiopyran-2-carbothioamide-1-oxide, which is known as RP 49356 and is a potassium channel activator antihypertensive agent.

EP-A-273262 (Merck Patent GmbH), and EP-A-277611 and EP-A-277612 (Hoechst Aktiengesellschaft) describe classes of benzopyran derivatives which are potassium channel activator antihypertensive agents.

Atenolol, Pindolol and Propanolol are beta adrenergic blockers ($\beta$-blockers) having antihypertensive activity of formulae (A), (B) and (C):

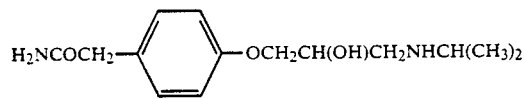
(A)

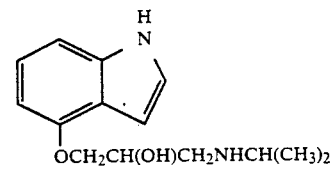
(B)

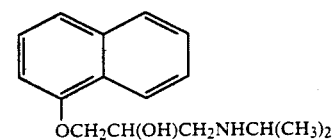
(C)

which are disclosed in Drugs, 31, (1986); Drugs of the Future, 10(11), 948 (1985); and Drugs of the Future 6(11), 731 (1981), respectively.

It has now been found that a combination of a potassium channel activator antihypertensive agent, such as pinacidil, RP 49536 or a benzopyran or pyranopyridine as hereinbefore referred to, and $\beta$-blocker antihypertensive agent, such as a compound of formula (A), (B) or (C), or a pharmaceutically acceptable salt of any of the foregoing has good antihypertensive activity. The effectiveness of the combination is greater than could be predicted from a consideration of the antihypertensive activities of the individual components and it appears that a synergistic effect is being produced.

Accordingly, the present invention provides a pharmaceutical product comprising a potassium channel activator antihypertensive agent, such as pinacidil, RP 49356 or a compound of formula (I), or a pharmaceutically acceptable salt thereof:

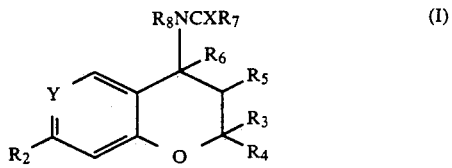

wherein
either Y is N and $R_2$ is hydrogen; or
Y is C—$R_1$
wherein
either one of $R_1$ and $R_2$ is hydrogen and the other is nitro, cyano, halo, $CF_3$, formyl, $NO_2$—CH=CH—, NC—CH=CH—; a group $R_xA^1$— wherein $R_x$ is $C_{1-6}$ alkyl, aryl or heteroaryl either of which may be optionally substituted by one, two or three of $C_{1-4}$ alkyl, $C_{1-4}$ alkoxy, nitro, halo, $CF_3$ and cyano; and $A^1$ is C=O, O.C=O, C=O.O, CHOH, SO, $SO_2$, O.SO, O.$SO_2$, CONH, O.CONH, C=S, O.C=S, C=S.O, CH.SH, SONH, $SO_2$NH, O.SONH, O.$SO_2$NH, CO—CH=CH, C=NHOH, C=$NNH_2$; or a group $R_yR_zNA^2$ wherein $R_y$ and $R_z$ are independently hydrogen or $C_{1-6}$ alkyl and $A^2$ is C=O, SO or $SO_2$; or $R_1$ is a $C_{3-8}$ cycloalkyl group or a $C_{1-6}$ alkyl group optionally substituted by a group $R_9$ which is hydroxy, $C_{1-6}$ alkoxy, amino optionally substituted by one or two $C_{1-6}$ alkyl groups, $C_{1-7}$ alkanoylamino, $C_{3-8}$ cycloalkyloxy or $C_{3-8}$ cycloalkylamino and $R_2$ is hydrogen; or one of $R_1$ and $R_2$ is nitro, cyano or $C_{1-3}$ alkylcarbonyl and the other is a different group selected from nitro, cyano, halo, $C_{1-3}$ alkylcarbonyl, methoxy or amino optionally substituted by one or two $C_{1-6}$ alkyl or by $C_{2-7}$ alkanoyl;

either one of $R_3$ and $R_4$ is hydrogen or $C_{1-4}$ alkyl and the other is $C_{1-4}$ alkyl; or $R_3$ and $R_4$ together are $C_{2-5}$ polymethylene;

either $R_5$ is hydrogen, hydroxy, $C_{1-6}$ alkoxy, $C_{1-7}$ acyloxy or $ONO_2$; and $R_6$ is hydrogen; or $R_5$ and $R_6$ together are a bond;

either $R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl; aryl or heteroaryl either being optionally substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups; and $R_8$ is hydrogen or $C_{1-6}$ alkyl; or $R_7$ and $R_8$ are joined together to form $C_{3-4}$ polymethylene optionally substituted by one or two $C_{1-6}$ alkyl groups or —CH$_2$—(CH$_2$)$_n$—Z—(CH$_2$)$_m$— wherein m and n are integers 0 to 2 such that m+n is 1 or 2 and Z is oxygen, sulphur or NR$_{10}$ wherein R$_{10}$ is hydrogen, C$_{1-9}$ alkyl, C$_{2-7}$ alkanoyl, phenyl C$_{1-4}$ alkyl, naphthylcarbonyl, phenylcarbonyl or benzylcarbonyl optionally substituted in the phenyl or naphthyl ring by one or two C$_{1-6}$ alkyl, C$_{1-6}$ alkoxy or halogen; mono- or bi-cyclic heteroarylcarbonyl; or R$_7$ and R$_8$ are joined to form —B$^1$=B$^2$—B$^3$=B$^4$— wherein one of B$^1$ to B$^4$ is CH or N and the other three are CH;

X is oxygen or sulphur; and the R$_8$NCXR$_7$ moiety is trans to the R$_5$ group when R$_5$ is hydroxy, C$_{1-6}$ alkoxy or C$_{1-7}$ acyloxy;

and β-blocker antihypertensive agent, such as a compound of formula (A), (B) or (C), or a pharmaceutically acceptable salt thereof:

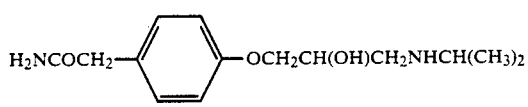  (A)

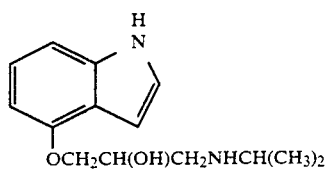  (B)

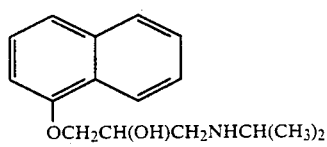  (C)

as a combined preparation for simultaneous, separate or sequential use in therapy of hypertension.

In a preferred aspect, the active components of the product are administered simultaneously.

The present invention further provides a pharmaceutical composition comprising a potassium channel activator antihypertensive agent, such as pinacidil, RP 49536 or a compound of formula (I), or a pharmaceutically acceptable salt thereof and β-blocker antihypertensive agent, such as a compound of formula (A), (B) or (C), or a pharmaceutically acceptable salt thereof; in combination with a pharmaceutically acceptable carrier.

The invention yet further provides the use of a potassium channel activator antihypertensive agent, such as pinacidil, RP 49356 or a compound of formula (I) or a pharmaceutically acceptable salt thereof and a β-blocker antihypertensive agent, such as a compound of formula (A), (B) or (C), or a pharmaceutically acceptable salt thereof, or a pharmaceutically acceptable salt thereof, in the manufacture of a pharmaceutical preparation for simultaneous, separate or sequential use in antihypertensive therapy.

Suitable and preferred values for the variable groups or atoms in formula (I) are as described for the corresponding variables in EP-A-76075, 91748, 93535, 95316, 107423, 120426, 120427, 126311, 126350, 126367, 138134, 205292, 214818 and 250077. Corresponding U.S. Patent references are U.S. Pat. Nos. 4,446,113, 4,542,149, 4,510,152, 4,481,214, 4,496,565, 4,555,509, 4,610,992, 4,571,406, 4,629,734, 4,575,511, 4,677,116 and U.S. Ser. Nos. 871711, 902428 and 045626, respectively.

All C$_{1-6}$ alkyl or alkyl containing groups in formula (I) are preferably selected from methyl, ethyl, n- and iso-propyl, n-, iso-, sec- and tert-butyl.

C$_{3-8}$ cycloalkyl groups are cyclopropyl, cyclobutyl, cyclopentyl, cyclohexyl, cycloheptyl and cyclooctyl.

Aryl includes phenyl and naphthyl.

Heteroaryl includes a 5- or 6-membered monocyclic or 9- or 10-membered bicyclic of which 5- or 6-membered monocyclic heteroaryl is preferred. In addition 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazolyl and triazolyl. Preferred examples of such groups include furanyl, thienyl, pyrryl and pyridyl, in particular 2- and 3-furyl, 2- and 3-pyrryl, 2- and 3-thienyl and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolyl. Preferred examples of such groups include 2- and 3-benzofuryl, 2- and 3-benzothienyl, and 2- and 3-indolyl, and 2- and 3-quinolyl.

Suitable examples of groups or atoms for optional substitution of aryl and heteroaryl include one, two or three substituents independently selected from C$_{1-4}$ alkyl, C$_{1-4}$ alkoxy, halo (such as fluoro, chloro, bromo), hydroxy, nitro and cyano.

Acyl groups are preferably carboxylic acyl, usually alkanoyl.

A particularly preferred compound of formula (I) is the compound of Example 1 of EP-A-76075 and U.S. Pat. No. 4,446,113, (±)-6-cyano-3,4-dihydro-2,2-dimethyl-trans-4-(2-oxo-1-pyrrolidinyl)-2H-benzo[b]-pyran-3-ol, also known as cromakalim; and its (−)-enantiomer, BRL 38227, disclosed in EP-A-120428.

Examples of pharmaceutically acceptable salts of the compounds of formula (I) are as described in the aforementioned European Patent references, the subject matter of which is incorporated herein by reference. A particularly preferred example of a salt of the compounds of formula (A), (B) or (C) is the hydrochloride salt.

It will be appreciated that the compounds of formula (I) wherein R$_5$ is hydroxy, alkoxy or acyloxy have an asymmetric centre at the 3- and 4- carbon atoms, and are capable of existing in the (3R, 4S) and (3S, 4R) forms. The invention extends to each of these forms including racemates. The (3S, 4R) form is preferred.

The above described products and compositions have blood pressure lowering activity, and are potentially useful in the treatment of hypertension.

The compounds of formula (I), and salts thereof may be prepared as described in the aforementioned European and U.S. Patent references.

Pinacidil and RP 49536, and salts thereof may be prepared as described in the appropriate aforementioned patent publications.

The product of the invention may be administered by the oral route to humans and may be compounded in the form of syrup, tablets or capsule for either separate, sequential or simultaneous administration.

However, they may be adapted for other modes of administration, for example parenteral administration for patients suffering from heart failure. Other alternative modes of administration include sublingual or transdermal administration.

Generally, compositions containing from about 0.5 to 25 mg of a compound of formula (A), (B) or (C), or a pharmaceutically acceptable salt thereof per mg of pinacidil, RP 49536 or a compound of formula (I) or a pharmaceutically acceptable salt thereof are effective, depending on the activity of the potassium channel activator.

In order to obtain consistency of administration it is preferred that a composition of the invention is in the form of a unit-dose. Suitable unit dose forms include tablets, capsules and powders in sachets or vials. Such unit dose forms may contain a total of from 0.5 to 100 mg of the potassium channel activator and more usually from 0.5 to 50 mg, for example 0.5 to 25 mg such as 0.5, 1, 2, 3, 5, 10, 15 or 20 mg. The unit dose form will normally contain from about 5 to 100 mg of the $\beta$-blocker, more usually 10 to 50 mg, for example 10, 15, 20, 25, 30 mg. Such compositions may be administered from 1 to 6 times a day, more usually from 2 to 4 times a day, in a manner such that the daily dose of potassium channel activator is from 0.5 to 200 mg for a 70 kg human adult and more particularly from 0.5 to 25 mg, and the daily dose of the $\beta$-blocker is from 10 to 500 mg for a 70 kg human adult and more particularly from 10 to 100 mg.

With the above indicated dosage range, no adverse toxicological effects are indicated with the composition of the invention.

The compositions of the invention may be formulated with conventional excipients, such as a filler, a disintegrating agent, a binder, a lubricant, a flavouring agent. They are formulated in conventional manner, for example in a manner similar to that used for anti-hypertensive agents.

It is greatly preferred that the potassium channel activator antihypertensive agent, such as pinacidil, RP 49536 or the compound of formula (I) or a pharmaceutically acceptable salt thereof and the $\beta$-blocker antihypertensive agent, such as the compounds of formula (A), (B) or (C), or a pharmaceutically acceptable salt thereof are administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as other classes of anti-hypertensive agents and diuretics.

As is common practice, the compositions will usually be accompanied by written or printed directions for use in the medical treatment concerned.

It will be appreciated that each component of the product of the invention may be administered by a different route.

The present invention yet further provides a method of treating hypertension in mammals including man, which comprises administering to the suffering mammal an anti-hypertensive effective amount of a pharmaceutical composition comprising a potassium channel activator antihypertensive agent, such as pinacidil, RP 49536 or a compound of formula (I) or a pharmaceutically acceptable salt thereof and $\beta$-blocker antihypertensive agent, such as a compound of formula (A), (B) or (C), or a pharmaceutically acceptable salt thereof, in combination with a pharmaceutically acceptable carrier.

The following pharmacological data illustrate the invention.

PHARMACOLOGICAL DATA

Potentiation of the anti-hypertensive response to potassium channel activators has been observed in conscious male spontaneously hypertensive rats (SHR) where the potassium channel activator compounds were combined with the β-blocker atenolol.

Mean arterial blood pressures were measured from an indwelling catheter as described by Buckingham 1976 J. Pharm. Pharmac Vol. 28, pp 459–461.

The results are as shown in Table I.

Notes

1. Calculation of area under the control group blood pressure curve (AUC).

Group mean arterial blood pressure values were calculated as % change from the pretreatment baseline. For each drug treatment group the area under the control group blood pressure curve was calculated using a trapezoidal method. In the table AUC values are given for the time intervals 0-2h and 0-4h. Predicted AUC values were arrived at by combining values for each treatment given alone.

TABLE I

| TREATMENT | DOSE (mg/kg po) | n | AUC (0-2 h) | (Predicted AUC) | AUC (0-4 h) | (Predicted AUC) |
|---|---|---|---|---|---|---|
| Atenolol | 10 | 10 | 660 | | 2356 | |
| Cromakalim | 0.075 | 10 | 1941 | | 2981 | |
|  | 0.1 | 11 | 2518 | | 3763 | |
|  | 0.15 | 10 | 3798 | | 6029 | |
| Atenolol + | 10 | | | | | |
| Cromakalim | 0.075 | 9 | 3611 | (2601) | 7169 | (5337) |
|  | 0.1 | 10 | 4215 | (3178) | 8158 | (6119) |
|  | 0.15 | 10 | 4839 | (4458) | 9099 | (8385) | n = number of animals per treatment.
AUC = area under the control group blood pressure curve.

We claim:

1. A pharmaceutical composition for use in the treatment of hypertension in mammals including humans, comprising an antihypertensively effective amount of a potassium channel activator antihypertensive agent and a synergistically effective amount of a β-blocker antihypertensive agent, in combination with a pharmaceutically acceptable carrier.

2. A composition according to claim 1 wherein the potassium channel activator antihypertensive agent is pinacidil, RP 49356 or a compound of the formula (I):

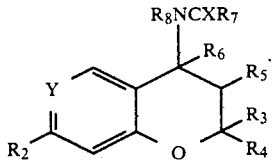

or a pharmaceutically acceptable salt thereof wherein either Y is N and $R_2$ is hydrogen; or Y is C—$R_1$ wherein either one of $R_1$ and $R_2$ is hydrogen and the other is nitro, cyano, halo, $CF_3$, formyl, $NO_2$—CH=CH—, NC—CH=CH—; $R_xA^1$— wherein $R_x$ is alkyl of 1 to 6 carbon atoms, unsubstituted or substituted phenyl, unsubstituted or substituted naphthyl, or an unsubstituted or substituted 5- or 6-membered monocylic or a 9- or 10- membered bicyclic ring which rings contain up to 3 heteroatoms selected from the group consisting of oxygen, nitrogen, and sulphur wherein the substituents are selected from the group consisting of 1, 2, or 3 alkyl of 1 to 4 carbon atoms, alkoxy of 1 to 4 carbon atoms, nitro, halo, $CF_3$ and cyano; and $A^1$ is C=O, O.C=O, C=O.O, CHOH, SO, $SO_2$, O.SO, O.$SO_2$, CONH, O.CONH, C=S, O.C=S, C=S.O, CH.SH, SONH, $S_2ONH$, O.SONH, O.-$SO_2$NH, CO—CH=CH, C=NHOH, and C=$NNH_2$; or $R_yR_zNA^2$ wherein $R_y$ and $R_z$ are each hydrogen or alkyl of 1 to 6 carbon atoms and $A^2$ is C=O, SO or $SO_2$; or $R_1$ is cycloalkyl of 3 to 8 carbon atoms or alkyl of 1 to 6 carbon atoms unsubstituted or substituted by $R^9$ wherein $R_9$ is hydroxy, alkoxy of 1 to 6 carbon atoms, amino unsubstituted or substituted by one or two alkyl moieties of 1 to 6 carbon atoms, alkanoylamino of 1 to 7 carbon atoms, cycloalkyloxy of 3 to 8 carbon atoms or cycloalkylamino of 3 to 8 carbon atoms and $R^2$ is hydrogen; or one of $R_1$ and $R_2$ is nitro, cyano or alkylcarbonyl of 1 to 3 carbon atoms in the alkyl moiety and the other is a different moiety selected from the group consisting of nitro, cyano, halo, alkylcarbonyl of 1 to 3 carbon atoms in the alkyl moiety, methoxy or amino unsubstituted or substituted by one or two alkyl moieties of 1 to 6 carbon atoms or by alkanoyl of 2 to 7 carbon atoms in the alkyl moiety;

either one of $R_3$ and $R_4$ is hydrogen or alkyl of 1 to 4 carbon atoms and the other is alkyl of 1 to 4 carbon atoms; or $R_3$ and $R_4$ together are polymethylene of 2 to 5 carbon atoms;

either $R_5$ is hydrogen, hydroxy, alkoxy of 1 to 6 carbon atoms, acyloxy of 1 to 7 carbon atoms or $ONO_2$; and $R_6$ is hydrogen; or $R_5$ and $R_6$ together are a bond;

either $R_7$ is hydrogen, alkyl of 1 to 6 carbon atoms unsubstituted or substituted by hydroxy, alkoxy of 1 to 6 carbon atoms, alkoxycarbonyl of 1 to 6 carbon atoms in the alkoxy moiety or carboxy, alkyl of 1 to 6 carbon atoms substituted by halo, or alkenyl of 2 to 6 carbon atoms; phenyl, naphthyl or a 5- or 6-membered monocyclic or a 9- or 10- membered bicyclic ring which contains up to three heteroatoms selected from the group consisting of oxygen, nitrogen and sulphur, said phenyl, said naphthyl and said monocyclic or bicyclic ring being unsubstituted or substituted by up to 3 substituents selected from the group consisting of alkoxy or 1 to 6 carbon atoms, hydroxy, halo, trifluoromethyl, nitro, cyano, carboxylic acyl of 1 to 12 carbon atoms, and amino or aminocarbonyl unsubstituted or substituted by 1 or 2 alkyl moieties of 1 to 6 carbon atoms; and $R_8$ is hydrogen or alkyl of 1 to 6 carbon atoms; or $R_7$ and $R_8$ together are polymethylene of 3 or 4 carbon atoms unsubstituted or substituted by 1 or 2 alkyl moieties of 1 to 6 carbon atoms or $-CH_2-(CH_2)_n-Z-(CH_2)_m-$ wherein m and n are integers from 0 to 2 such that m+n is 1 or 2 and Z is oxygen, sulphur or $NR_{10}$ wherein $R_{10}$ is hydrogen, alkyl of 1 to 9 carbon atoms, alkanoyl of 2 to 7 carbon atoms in the alkyl moiety, phenylalkyl of 1 to 4 carbon atoms in the alkyl moiety, naphthylcarbonyl, phenylcarbonyl or benzylcarbonyl unsubstituted or substituted in the phenyl or naphthyl moiety by one or two alkyl moieties of 1 to 6 carbon atoms, alkoxy moieties of 1 to 6 carbon atoms, or halo; mono- or bi-cyclic heteroarylcarbonyl wherein the heteroaryl moiety is a 5- or 6-membered monocyclic ring or a 9- or 10-bicyclic ring having up to three heteroatoms selected from the group consisting of oxygen, nitrogen and sulfur; or $R_7$ and $R_8$ together form $-B^1=B^2-B^3=B^4-$ wherein one of $B^1$ to $B^4$ is CH or N and the other three are CH;

X is oxygen or sulphur; and the moiety $R_8NCXR_7$ is trans to the $R_5$ group when $R_5$ is hydroxy, alkoxy of 1 to 6 carbon atoms or acyloxy of 1 to 7 carbon atoms; and the β-blocker antihypertensive agent is a compound of the formula (A), (B) or (C),

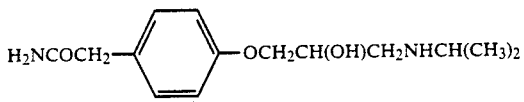
(A)

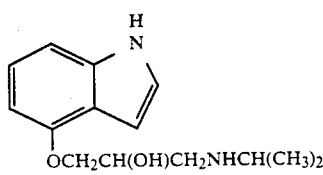
(B)

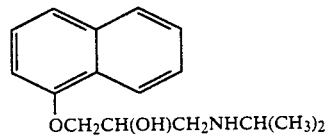
(C)

or a pharmaceutically acceptable salt thereof.

3. A composition according to claim 2 wherein $R_3$ and $R_4$ are both methyl groups.

4. A composition according to claim 2 wherein the potassium channel activator antihypertensive agent is of the formula (I) wherein Y is N or $C-R_1$ wherein $R_1$ is alkyl of 1 to 6 carbon atoms, $CF_3$, nitro, cyano or alkylcarbonyl of 1 to 3 carbon atoms in the alkyl moiety, and $R_2$ is hydrogen.

5. A composition according to claim 2 wherein $R_7$ and $R_8$ together are polymethylene of 3 or 4 carbon atoms, $-CH_2-(CH_2)_n-Z-(CH_2)_m-$ or $B^1=B^2-B^3=B^4$ wherein one of $B^1$ to $B^4$ is CH or N and the other 3 are CH, m and n are integers from 0 to 2 such that m+n is 1 or 2 and Z is oxygen sulphur or $NR_{10}$ wherein $R_{10}$ is hydrogen, alkyl of 1 to 9 carbon atoms, alkanoyl of 2 to 7 carbon atoms in the alkyl moiety, phenylalkyl of 1 to 4 carbon atoms in the alkyl moiety, naphthyl carbonyl, phenyl-carbonyl or benzyl-carbonyl unsubstituted or substituted in the phenyl or naphthyl ring by 1 or 2 alkyl moieties of 1 to 6 carbon atoms, alkoxy moieties of 1 to 6 carbon atoms or halo; or $R_8$ is hydrogen or methyl and $R_7$ is ethyl, methyl, hydrogen or phenyl unsubstituted or substituted by 1, 2, 3 or 4 substituents selected from the group consisting of methyl, methoxy, hydroxy, fluoro and chloro.

6. A composition according to claim 5 wherein the compound of formula (I) is (±)-6-cyano-3,4-dihydro-2,2-dimethyl-trans-4-(2-oxo-1-pyrrolidinyl)-2H-benzo[b]pyran-3-ol, or the (−)-enantiomer thereof.

7. A composition according to claim 2, containing 0.5 to 25 mg of a compound of formula (A), (B), or (C) per mg of pinacidil, RP 49356 or a compound of formula (I), or a pharmaceutically acceptable salt thereof.

8. A composition according to claim 1 wherein the potassium channel activator antihypertensive agent is (±)-6-cyano -3,4-dihydro-2,2-dimethyl-trans-4-(2-oxo-1-pyrrolidinyl)-2H-benzo[b]pyran-3-ol or the (−)-enantiomer thereof and the β-blocker antihypertensive agent is Atenolol.

9. A method of treating hypertension in mammals including humans which comprises administering to a mammal in need thereof an antihypertensively effective amount of a potassium channel activator antihypertensive agent and a synergistically effective amount of a β-blocker antihypertensive agent, in combination with a pharmaceutically acceptable carrier.

10. A method according to claim 9 wherein the administration is together.

11. A method according to claim 9 wherein the administration is sequential.

12. A method according to claim 9 wherein the potassium channel activator antihypertensive agent is (±)-6-cyano -3,4-dihydro-2,2-dimethyl-trans-4-(2-oxo-1-pyrrolidinyl)-2H-benzo[b]pyran-3-ol or the (−)-enantiomer thereof and the β-blocker antihypertensive agent is Atenolol.

13. A method according to claim 9 wherein the potassium channel activator antihypertensive agent is pinacidil, RP 49356 or a compound of the formula (I):

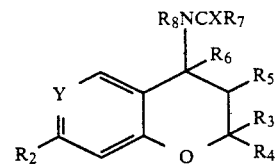

or a pharmaceutically acceptable salt thereof wherein either Y is N and $R_2$ is hydrogen; or Y is C—$R_1$ *wherein either one of* $R_1$ and $R_2$ is hydrogen and the other is nitro, cyano, halo, $CF_3$, formyl, $NO_2-CH=CH-$, $NC-CH=CH-$; $R_xA^1-$ wherein $R_x$ is alkyl of 1 to 6 carbon atoms, unsubstituted or substituted phenyl, unsubstituted or substituted naphthyl, or an unsubstituted or substituted 5- or 6-membered monocylic or a 9- or 10-membered bicyclic ring which rings contain up to 3 heteroatoms selected from the group consisting of oxygen, nitrogen, and sulphur wherein the substituents are selected from the group consisting of 1, 2, or 3 alkyl of 1 to 4 carbon atoms, alkoxy of 1 to 4 carbon atoms, nitro, halo, $CF_3$ and cyano; and $A^1$ is $C=O$, $O.C=O$, $C=O.O$, CHOH, SO, $SO_2$, O.SO, $O.SO_2$, CONH, O.CONH, $C=S$, $O.C=S$, C=S.O, CH.SH, SONH, S₂ONH, O.SONH, O.-SO₂NH, CO—CH=CH, C=NHOH, and C=NNH₂; or $R_y R_z NA^2$ wherein $R_y$ and $R_z$ are each hydrogen or alkyl of 1 to 6 carbon atoms and $A^2$ is C=O, SO or SO₂; or $R_1$ is cycloalkyl of 3 to 8 carbon atoms or alkyl of 1 to 6 carbon atoms unsubstituted or substituted by $R^9$ wherein $R_9$ is hydroxy, alkoxy of 1 to 6 carbon atoms, amino unsubstituted or substituted by one or two alkyl moieties of 1 to 6 carbon atoms, alkanoylamino of 1 to 7 carbon atoms, cycloalkyloxy of 3 to 8 carbon atoms or cycloalkylamino of 3 to 8 carbon atoms and $R^2$ is hydrogen; or one of $R_1$ and $R_2$ is nitro, cyano or alkylcarbonyl of 1 to 3 carbon atoms in the alkyl moiety and the other is a different moiety selected from the group consisting of nitro, cyano, halo, alkylcarbonyl of 1 to 3 carbon atoms in the alkyl moiety, methoxy or amino unsubstituted or substituted by one or two alkyl moieties of 1 to 6 carbon atoms or by alkanoyl of 2 to 7 carbon atoms in the alkyl moiety;

either one of $R_3$ and $R_4$ is hydrogen or alkyl of 1 to 4 carbon atoms and the other is alkyl of 1 to 4 carbon atoms; or $R_3$ and $R_4$ together are polymethylene of 2 to 5 carbon atoms;

either $R_5$ is hydrogen, hydroxy, alkoxy of 1 to 6 carbon atoms, acyloxy of 1 to 7 carbon atoms or ONO₂; and $R_6$ is hydrogen; or $R_5$ and $R_6$ together are a bond;

either $R_7$ is hydrogen, alkyl of 1 to 6 carbon atoms unsubstituted or substituted by hydroxy, alkoxy of 1 to 6 carbon atoms, alkoxycarbonyl of 1 to 6 carbon atoms in the alkoxy moiety or carboxy, alkyl of 1 to 6 carbon atoms substituted by halo, or alkenyl of 2 to 6 carbon atoms; phenyl, naphthyl or a 5- or 6-membered monocyclic or a 9- or 10- membered bicyclic ring which contains up to three heteroatoms selected from the group consisting of oxygen, nitrogen and sulphur, said phenyl, said naphthyl and said monocyclic or bicyclic ring being unsubstituted or substituted by up to 3 substituents selected from the group consisting of alkoxy or 1 to 6 carbon atoms, hydroxy, halo, trifluoromethyl, nitro, cyano, carboxylic acyl of 1 to 12 carbon atoms, and amino or aminocarbonyl unsubstituted or substituted by 1 or 2 alkyl moieties of 1 to 6 carbon atoms; and $R_8$ is hydrogen or alkyl of 1 to 6 carbon atoms; or $R_7$ and $R_8$ together are polymethylene of 3 or 4 carbon atoms unsubstituted or substituted by 1 or 2 alkyl moieties of 1 to 6 carbon atoms or —CH₂—(CH₂)ₙ—Z—(CH2)ₘ— wherein m and n are integers from 0 to 2 such that m+n is 1 or 2 and Z is oxygen sulphur or NR₁₀ wherein R₁₀ is hydrogen, alkyl of 1 to 9 carbon atoms, alkanoyl of 2 to 7 carbon atoms in the alkyl moiety, phenylalkyl of 1 to 4 carbon atoms in the alkyl moiety, naphthylcarbonyl, phenylcarbonyl or benzylcarbonyl unsubstituted or substituted in the phenyl or naphthyl moiety by one or two alkyl moieties of 1 to 6 carbon atoms, alkoxy moieties of 1 to 6 carbon atoms, or halo; mono- or bi-cyclic heteroarylcarbonyl wherein the heteroaryl moiety is a 5- or 6-membered monocyclic ring or a 9- or 10-bicyclic ring having up to three heteroatoms selected from the group consisting of oxygen, nitrogen and sulfur; or $R_7$ and $R_8$ together form —B¹=B²—B³=B⁴— wherein one of B¹ to B⁴ is CH or N and the other three are CH;

X is oxygen or sulphur; and the moiety R₈NCXR₇ is trans to the $R_5$ group when $R_5$ is hydroxy, alkoxy of 1 to 6 carbon atoms or acyloxy of 1 to 7 carbon atoms; and the β-blocker antihypertensive agent is a compound of the formula (A), (B) or (C),

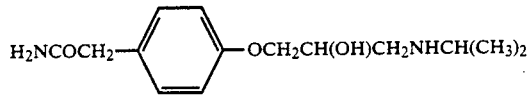

(A)

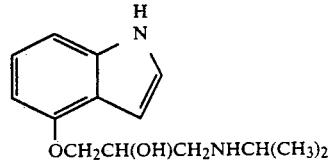

(B)

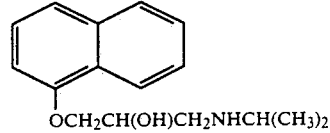

(C)

or a pharmaceutically acceptable salt thereof.

14. A method according to claim 13 wherein the potassium channel activator antihypertensive agent is of the formula (I) wherein Y is N or C—R₁ wherein R₁ is alkyl of 1 to 6 carbon atoms, CF₃, nitro, cyano or alkylcarbonyl of 1 to 3 carbon atoms in the alkyl moiety, and R₂ is hydrogen.

15. A method according to claim 13 wherein R₃ and R₄ are both methyl groups.

16. A method according to claim 13 wherein R₇ and R₈ together are polymethylene of 3 or 4 carbon atoms, —CH₂—(CH₂)ₙ—Z—(CH2)ₘ— or B¹=B²=B³=B⁴ wherein one of B¹ to B⁴ is CH or N and the other 3 are CH, m and n are integers from 0 to 2 such that m+n is 1 or 2 and Z is oxygen sulphur or NR₁₀ wherein R₁₀ is hydrogen, alkyl of 1 to 9 carbon atoms; alkanoyl of 2 to 7 carbon atoms in the alkyl moiety, phenylalkyl of 1 to 4 carbon atoms in the alkyl moiety, naphthyl carbonyl, phenylcarbonyl or benzylcarbonyl unsubstituted or substituted in the phenyl or naphthyl ring by 1 or 2 alkyl moieties of 1 to 6 carbon atoms, alkoxy moieties of 1 to 6 carbon atoms or halo; or R₈ is hydrogen or methyl and R₇ is ethyl, methyl, hydrogen or phenyl unsubstituted or substituted by 1, 2, 3 or 4 substituents selected from the group consisting of methyl, methoxy, hydroxy, fluoro and chloro.

17. A composition according to claim 13 wherein the compound of formula (I) is (±)-6-cyano-3,4-dihydro-2,2-dimethyl-trans-4-(2-oxo-1-pyrrolidinyl)-2H-benzo[b]pyran-3-ol or the (−)-enantiomer thereof.

* * * * *